US008247603B2

(12) United States Patent
Alken et al.

(10) Patent No.: US 8,247,603 B2
(45) Date of Patent: Aug. 21, 2012

(54) DEUTERATED CATECHOLAMINE DERIVATIVES AND MEDICAMENTS COMPRISING SAID COMPOUNDS

(75) Inventors: Rudolf-Giesbert Alken, Sjoedala Gard (SE); Frank Schneider, Berlin (DE)

(73) Assignee: Birds Pharma GmbH Berolina Innovative, Berlin (DE)

( * ) Notice: Subject to any disclaimer, the term of this patent is extended or adjusted under 35 U.S.C. 154(b) by 866 days.

(21) Appl. No.: 12/224,120

(22) PCT Filed: Feb. 16, 2007

(86) PCT No.: PCT/EP2007/001555
§ 371 (c)(1),
(2), (4) Date: Aug. 18, 2008

(87) PCT Pub. No.: WO2007/093450
PCT Pub. Date: Aug. 23, 2007

(65) Prior Publication Data
US 2009/0018191 A1     Jan. 15, 2009

(30) Foreign Application Priority Data
Feb. 17, 2006  (DE) .......................... 10 2006 008 316

(51) Int. Cl.
C07B 59/00 (2006.01)
C07C 229/08 (2006.01)
A61P 25/00 (2006.01)
A61K 31/198 (2006.01)

(52) U.S. Cl. ............... 562/446; 560/37; 560/38; 560/39; 560/40

(58) Field of Classification Search .................. None
See application file for complete search history.

(56) References Cited

U.S. PATENT DOCUMENTS

| | | | | |
|---|---|---|---|---|
| 5,017,607 A * | 5/1991 | Chiesi | ............................ | 514/534 |
| 5,525,631 A * | 6/1996 | Milman et al. | ................. | 514/567 |
| 6,221,335 B1 * | 4/2001 | Foster | ........................... | 424/1.81 |
| 6,440,710 B1 * | 8/2002 | Keinan et al. | ................... | 435/148 |
| 6,603,008 B1 * | 8/2003 | Ando et al. | ................. | 546/269.7 |
| 2006/0135615 A1 * | 6/2006 | Alken | ............................ | 514/567 |

FOREIGN PATENT DOCUMENTS

| | | |
|---|---|---|
| DE | 2 049 115 A1 | 4/1972 |
| DE | 102 61 807 A1 | 7/2004 |
| WO | WO 2004/056306 A2 | 7/2004 |
| WO | WO 2004/056724 A1 | 7/2004 |

OTHER PUBLICATIONS

Dewar et al. Neuro-Psychopharmacology & Biological Psychiatry 1985, 9(5-6), 675-680.*
Weiner et al. Neurology, 2000, 54(7), p. 1538.*
Claffey et al. Chem Res. Toxicol. 2001, 14, 1339-1334.*
Yu Biochemistry and Cell biology, 1988, v66(8), 853-861.*
Dyck Journal of Neurochemistry 1986, 46(2), pp. 399-404.*
Tonn et al. Biological Mass Spectrometry 1993, 22 (11), pp. 633-642.*
Haskins Biomedical Spectrometry 1982, 9(7), pp. 269-277.*
Wolen Journal of Clinical Pharmacology 1986; 26, pp. 419-424; abstract.*
Gouyette Biomedical and Environmental Mass Spectrometry, 1988, 15, pp. 243-247.*
Kushner et al., "Pharmacological uses and perspectives of heavy water and deuterated compounds," Can. J. Physiol. Pharmacol., 77:79-88 (1999).
Yu et al., "Stereospecific Deuterium Substitution at the alpha-Carbon Position of Dopamine and its Effect on Oxidative Deamination Catalyzed by MAO-A and MAO-B from Different Tissues," Biochemical Pharmacology, 35(6):1027-36 (1986).
Edwards et al., "Conversion of 3,4-Dihydroxyphenylalanine and Deuterated 3,4-Dihydroxyphenylalanine to Alcoholic Metabolites of Catecholamines in Rat Brain," Journal of Neurochemistry, 36(5):1641-7 (1981).
Dewar et al., "Changes in Brain Catecholamine Levels Following DL-Dopa are not Potentiated by Deuterium Substitution," Prog. Neuro-Psychopharmacol. & Biol. Psychiat., 9:675-80 (1985).
Stark et al., Quantitative Analysis of N-Phenylpropenoyl-L-amino Acids in Roasted Coffee and Cocoa Powder by Means of a Stable Isotope Dilution Assay, J. Agric. Food Chem., 54:2859-67 (2006).
Vining et al., "Deuterium Exchange Labelling of Biologically Important Phenols, Indoles and Steroids," Journal of Labelled Compounds and Radiopharmaceut., XVIII:1683-92 (1981).

* cited by examiner

*Primary Examiner* — Yevegeny Valenrod
(74) *Attorney, Agent, or Firm* — Davidson, Davidson & Kappel, LLC

(57) ABSTRACT

The present invention concerns deuterated catecholamine derivatives as well as pharmaceuticals containing these compounds. In addition, the invention concerns the use of deuterated catecholamine derivatives as well as physiologically acceptable salts thereof, and also pharmaceutical compositions, which contain these compounds, also in combination with enzyme inhibitors, for the treatment of dopamine deficiency diseases or diseases which are based on disrupted tyrosine transport or disrupted tyrosine decarboxylase, as well as other disorders.

18 Claims, No Drawings

DEUTERATED CATECHOLAMINE DERIVATIVES AND MEDICAMENTS COMPRISING SAID COMPOUNDS

The invention concerns deuterated catecholamine derivatives as well as pharmaceuticals containing these compounds.

Know representatives of catecholamines, such as L-dopa (levodopa) as well as their carboxylic acid esters, are utilized, among other things, for the treatment of Parkinson's disease and restless leg syndrome. Such a pharmaceutical which contains levodopa is, for example, Dopaflex®. L-dopa acts on the dopamine concentration in neurons of the brain. Unlike dopamine itself, it can pass through the blood-brain barrier and is converted to dopamine in the brain.

In addition, levodopa is administered in combination with active additives in pharmaceuticals. Combinations of levodopa are used with peripheral decarboxylase inhibitors, with inhibitors of the enzyme catechol-O-methyltransferase (COMT), with inhibitors of the enzyme monoamine oxidase (MAO) and with dopamine β-hydroxylase inhibitors.

In this connection, the decarboxylase inhibitors used are, for example: D,L-serine 2-(2,3,4-trihydroxybenzyl) hydrazide (benserazide), (−)-L-α-hydrazino-3,4-dihydroxy-α-methylhydrocinnamic acid (carbidopa), L-serine-2-(2,3,4-trihydroxybenzyl) hydrazide, glycine-2-(2,3,4-trihydroxybenzyl) hydrazide and L-tyrosine-2-(2,3,4-trihydroxybenzyl) hydrazide. Examples of combination preparations of levodopa and decarboxylase inhibitors include, among others: Madopar® (levodopa and benserazide hydrochloride) as well as Nacom® (levodopa and carbidopa).

Examples of COMT inhibitors are entacapone (Comtan®) and cabergoline and frequently used MAO inhibitors are selegiline hydrochloride, moclobemide and tranylcypromine.

Calcium 5-butyl picolinate and calcium 5-pentyl picolinate are described as inhibitors for dopamine-β-hydroxylase (DE 2,049,115).

WO-A 2004/056724 discloses deuterated catecholamine having two deuterium atoms in the β-position. These compounds exhibit improved pharmacokinetic and/or pharmacodynamic properties with respect to undeuterated compounds and as compared to L-DOPA.

An object of the present invention is to prepare deuterated catecholamine derivatives, which have improved pharmacokinetic and/or pharmacodynamic properties when compared to compounds already known, as well as to prepare catecholamine derivatives, which can be utilized for the prophylaxis of psychoses including schizophrenia, and which can be used for producing pharmaceuticals for the prophylaxis of psychoses.

It has been surprisingly found that the deuterated catecholamine derivatives according to the invention have substantially better pharmacokinetic and/or pharmacodynamic properties than the undeuterated compounds and the β,β-dideuterated compounds known in the art and that they can also be utilized for the prophylaxis of psychoses and can be used for producing pharmaceuticals for the prophylaxis of psychoses.

According to the invention, the object is thus solved by the preparation of compounds of general formula I:

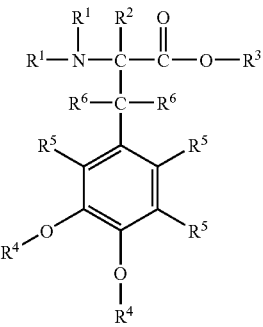

Formula I wherein
$R^1$ is H or D, or a group that is easily hydrolytically or enzymatically cleavable under physiological conditions,
$R^2$ indicates H or D,
$R^3$ is H, D, $C_1$ to $C_6$-alkyl or $C_5$ to $C_6$-cycloalkyl, deuterated $C_1$ to $C_6$-alkyl or $C_5$ to $C_6$-cycloalkyl, or a group that is easily hydrolytically or enzymatically cleavable under physiological conditions,
$R^4$ indicates H or D, or a group that is easily hydrolytically or enzymatically cleavable under physiological conditions,
$R^5$ is H or D, and
$R^6$ is H or D,
as well as their physiologically acceptable salts and their stereoisomers, enantiomeres or diastereomers in optically pure form.

Preferred are compounds according to general formula I wherein both residues R6 are not simultaneously Deuterium (D).

Groups that are easily hydrolytically or enzymatically cleavable under physiological conditions are known to one skilled in the art. The groups are common protective groups which are used in synthesis or that are such protective groups which lead to so-called prodrugs.

These groups may be selected from the group comprising methyl, perdeuteromethyl, ethyl, perdeuteroethyl, propyl, perdeuteropropyl, butyl, perdeuterobutyl, $C_1$ to $C_6$-alkyl, that may be branched or unbranched, or $C_5$ to $C_6$ cycloalkyl, deuterated or partly deuterated $C_1$ to $C_6$alkyl, that may be branched or unbranched, or deuterated or partly deuterated $C_5$ to $C_6$-cycloalkyl.

According to the invention deuterated catecholamine derivatives according to formula 1 are preferred, wherein
$R^1$ is H or D,
$R^2$ indicates H or D,
$R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D,
$R^5$ is D, and
$R^6$ is H or D, under the proviso that both residues $R^6$ are not simultaneously D.

Preferred are deuterated catecholamine derivatives according to formula 1, wherein
$R^1$ is H or D,
$R^2$ indicates D,
$R^3$ is D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D
$R^5$ is D, and
$R^6$ is H or D, under the proviso that both residues $R^6$ are not simultaneously D.

Preferred are also deuterated catecholamine derivatives according to formula 1, wherein
$R^1$ is H or D,
$R^2$ indicates D,
$R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D,
$R^5$ is D and
$R^6$ is H or D, under the proviso that both residues $R^6$ are not simultaneously D.

Preferred are deuterated catecholamine derivatives according to the general formula I, wherein
$R^1$ is H or D,
$R^2$ indicates D,
$R^3$ is $C_1$ to $C_6$-alkyl or $C_5$ to $C_6$-cycloalkyl,
$R^4$ indicates H or D,
$R^5$ is D, and
$R^6$ is H or D, under the proviso that both residues $R^6$ are not simultaneously D.

Preferred are deuterated catecholamine derivatives according to formula 1, wherein
$R^1$ is H or D,
$R^2$ indicates D,
$R^3$ is methyl,
$R^4$ indicates H or D,
$R^5$ is D, and
$R^6$ is H or D, under the proviso that both residues $R^6$ are not simultaneously D.

Preferred are deuterated catecholamine derivatives according to formula 1, wherein
$R^1$ is H or D,
$R^2$ indicates D,
$R^3$ is ethyl,
$R^4$ indicates H or D
$R^5$ is D, and
$R^6$ is H or D, under the proviso that both residues $R^6$ are not simultaneously D.

Preferred are deuterated catecholamine derivatives according to formula 1, wherein
$R^1$ is H or D,
$R^2$ indicates D,
$R^3$ is perdeuteroethyl,
$R^4$ indicates H or D
$R^5$ is D and,
$R^6$ is H or D, under the proviso that both residues $R^6$ are not simultaneously D.

Preferred are deuterated catecholamine derivatives according to formula 1, wherein
$R^1$ is H or D,
$R^2$ indicates H or D,
$R^3$ is perdeuteroethyl,
$R^4$ indicates H or D,
$R^5$ is D, and
$R^6$ is H or D, under the proviso that both residues $R^6$ are not simultaneously D.

Preferred are deuterated catecholamine derivatives according to formula 1, wherein
$R^1$ is H or D,
$R^2$ indicates H or D,
$R^3$ is perdeuteroethyl,
$R^4$ indicates D
$R^5$ is H or D, and
$R^6$ is H or D, under the proviso that both residues $R^6$ are not simultaneously D.

Preferred are deuterated catecholamine derivatives according to formula 1, namely
2-amino-2-deutero-3-(3,4-dihydroxyphenyl) propionic acid,
2-amino-2-deutero-3-(3,4-dihydroxyphenyl) propionic acid methyl ester,
2-amino-2-deutero-3-(3,4-dihydroxyphenyl) propionic acid ethyl ester,
D-2-amino-2-deutero-3-(3,4-dihydroxyphenyl) propionic acid,
D-2-amino-2-deutero-3-(3,4-dihydroxyphenyl) propionic acid methyl ester,
D-2-amino-2-deutero-3-(3,4-dihydroxyphenyl) propionic acid ethyl ester,
L-2-amino-2-deutero-3-(3,4-dihydroxyphenyl) propionic acid,
L-2-amino-2-deutero-3-(3,4-dihydroxyphenyl) propionic acid methyl ester,
L-2-amino-2-deutero-3-(3,4-dihydroxyphenyl) propionic acid ethyl ester,
D,L-2-amino-2-deutero-3-(3,4-dihydroxyphenyl) propionic acid,
D,L-2-amino-2-deutero-3-(3,4-dihydroxyphenyl) propionic acid methyl ester,
D,L-2-amino-2-deutero-3-(3,4-dihydroxyphenyl) propionic acid ethyl ester,
R/R-2-amino-2,3-dideutero-3-(3,4-dihydroxyphenyl) propionic acid,
R/R-2-amino-2,3-dideutero-3-(3,4-dihydroxyphenyl) propionic acid methyl ester,
R/R-2-amino-2,3-dideutero-3-(3,4-dihydroxyphenyl) propionic acid ethyl ester,
R/S-2-amino-2,3-dideutero-3-(3,4-dihydroxyphenyl) propionic acid,
R/S-2-amino-2,3-dideutero-3-(3,4-dihydroxyphenyl) propionic acid methyl ester,
R/S-2-amino-2,3-dideutero-3-(3,4-dihydroxyphenyl) propionic acid ethyl ester,
S/R-2-amino-2,3-dideutero-3-(3,4-dihydroxyphenyl) propionic acid,
S/R-2-amino-2,3-dideutero-3-(3,4-dihydroxyphenyl) propionic acid methyl ester,
S/R-2-amino-2,3-dideutero-3-(3,4-dihydroxyphenyl) propionic acid ethyl ester,
S/S-2-amino-2,3-dideutero-3-(3,4-dihydroxyphenyl) propionic acid,
S/S-2-amino-2,3-dideutero-3-(3,4-dihydroxyphenyl) propionic acid methyl ester,
S/S-2-amino-2,3-dideutero-3-(3,4-dihydroxyphenyl) propionic acid ethyl ester,
2-amino-2-deutero-3-(2,3,6-trideutero-4,5-dihydroxyphenyl) propionic acid,
2-amino-2-deutero-3-(2,3,6-trideutero-4,5-dihydroxyphenyl) propionic acid methyl ester,
2-amino-2-deutero-3-(2,3,6-trideutero-4,5-dihydroxyphenyl) propionic acid ethyl ester,
D-2-amino-2-deutero-3-(2,3,6-trideutero-4,5-dihydroxyphenyl) propionic acid,
D-2-amino-2-deutero-3-(2,3,6-trideutero-4,5-dihydroxyphenyl) propionic acid methyl ester,
D-2-amino-2-deutero-3-(2,3,6-trideutero-4,5-dihydroxyphenyl) propionic acid ethyl ester,
L-2-amino-2-deutero-3-(2,3,6-trideutero-4,5-dihydroxyphenyl) propionic acid,
L-2-amino-2-deutero-3-(2,3,6-trideutero-4,5-dihydroxyphenyl) propionic acid methyl ester,
L-2-amino-2-deutero-3-(2,3,6-trideutero-4,5-dihydroxyphenyl) propionic acid ethyl ester,
D,L-2-amino-2-deutero-3-(2,3,6-trideutero-4,5-dihydroxyphenyl) propionic acid, D,L-2-amino-2-deutero-3-(2,3,6-trideutero-4,5-dihydroxyphenyl) propionic acid methyl ester,
D,L-2-amino-2-deutero-3-(2,3,6-trideutero-4,5-dihydroxyphenyl) propionic acid ethyl ester,
2-amino-2,3-dideutero-3-(2,3,6-trideutero-4,5-dihydroxyphenyl) propionic acid,
2-amino-2,3-dideutero-3-(2,3,6-trideutero-4,5-dihydroxyphenyl) propionic acid methyl ester,
2-amino-2,3-dideutero-3-(2,3,6-trideutero-4,5-dihydroxyphenyl) propionic acid ethyl ester,
R/R-2-amino-2,3-dideutero-3-(2,3,6-trideutero-4,5-dihydroxyphenyl) propionic acid,
R/R-2-amino-2,3-dideutero-3-(2,3,6-trideutero-4,5-dihydroxyphenyl) propionic acid methyl ester,
R/R-2-amino-2,3-dideutero-3-(2,3,6-trideutero-4,5-dihydroxyphenyl) propionic acid ethyl ester,
R/S-2-amino-2,3-dideutero-3-(2,3,6-trideutero-4,5-dihydroxyphenyl) propionic acid,
R/S-2-amino-2,3-dideutero-3-(2,3,6-trideutero-4,5-dihydroxyphenyl) propionic acid methyl ester,
R/S-2-amino-2,3-dideutero-3-(2,3,6-trideutero-4,5-dihydroxyphenyl) propionic acid ethyl ester,
S/R-2-amino-2,3-dideutero-3-(2,3,6-trideutero-4,5-dihydroxyphenyl) propionic acid,
S/R-2-amino-2,3-dideutero-3-(2,3,6-trideutero-4,5-dihydroxyphenyl) propionic acid methyl ester,
S/R-2-amino-2,3-dideutero-3-(2,3,6-trideutero-4,5-dihydroxyphenyl) propionic acid ethyl ester,
S/S-2-amino-2,3-dideutero-3-(2,3,6-trideutero-4,5-dihydroxyphenyl) propionic acid,
S/S-2-amino-2,3-dideutero-3-(2,3,6-trideutero-4,5-dihydroxyphenyl) propionic acid methyl ester, and
S/S-2-amino-2,3-dideutero-3-(2,3,6-trideutero-4,5-dihydroxyphenyl) propionic acid ethyl ester.

Another embodiment of the invention is the use of the deuterated catecholamine derivatives according to the invention as well as physiologically acceptable salts thereof for the treatment of dopamine deficiency diseases or diseases which are based on disrupted tyrosine trans-port or disrupted tyrosine decarboxylase, such as Parkinson's disease, restless leg syndrome, dystonia, for the inhibition of prolactin secretion, for the stimulation of the release of growth hormone, for the treatment of neurological symptoms of chronic manganese intoxications, of amyotrophic lateral sclerosis and of multiple system atrophy.

Preferred is the use of deuterated catecholamine derivatives as well as physiologically acceptable salts thereof, in combination with an enzyme inhibitor or several enzyme inhibitors, for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy.

It is advantageous if the enzyme inhibitor or the enzyme inhibitors involve decarboxylase inhibitors and/or catechol-O-methyltransferase inhibitors and/or monoamine oxidase inhibitors and/or β-hydroxylase inhibitors.

It is particularly advantageous if the decarboxylase inhibitor is selected from the group consisting of the following: D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically acceptable salts thereof.

In particular, it is also advantageous if the catechol-O-methyltransferase inhibitor is selected from entacapone and cabergoline as well as physiologically acceptable salts thereof.

It is also preferred if the monoamine oxidase inhibitor is selected from the group consisting of selegiline, moclobemide and tranylcypromine, as well as physiologically acceptable salts thereof.

In addition, it is particularly preferred if the hydroxylase inhibitor is selected from calcium 5-butyl picolinate and calcium 5-pentyl picolinate as well as physiologically acceptable salts thereof.

Another subject of the invention is the use of the deuterated catecholamines according to the invention as well as physiologically acceptable salts thereof for the production of pharmaceuticals for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy.

Another subject of the present invention is a pharmaceutical composition which contains the deuterated catecholamines according to the invention as well as their physiologically acceptable salts for the treatment of dopamine deficiency diseases or diseases which are based on disrupted tyrosine transport or disrupted tyrosine decarboxylase, such as Parkinson's disease, restless leg syndrome, dystonia, for the inhibition of prolactin secretion, for stimulating the release of growth hormone, for the treatment of neurological symptoms of chronic manganese intoxications, of amyotrophic lateral sclerosis and of multiple system atrophy, in addition to pharmaceutically acceptable adjuvants and additives.

Particularly advantageous is a pharmaceutical composition which contains the deuterated catecholamines according to the invention as well as physiologically acceptable salts thereof for the treatment of Parkinson's disease, restless leg syndrome, dystonia, for the inhibition of prolactin secretion, for stimulating of the release of growth hormone, for the treatment of neurological symptoms of chronic manganese intoxications, of amyotrophic lateral sclerosis and of multiple system atrophy, as well as one or more enzyme inhibitors, in addition to pharmaceutically acceptable adjuvants and additives.

A pharmaceutical composition is particularly preferred in which the enzyme inhibitor or the enzyme inhibitors involve decarboxylase inhibitors and/or catechol-O-methyltransferase inhibitors and/or monoamine oxidase inhibitors and/or β-hydroxylase inhibitors.

Additionally preferred is a pharmaceutical composition in which the decarboxylase inhibitor is selected from the group consisting of D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically acceptable salts thereof.

Particularly advantageous is a pharmaceutical composition in which the catechol-O-methyltransferase inhibitor is selected from entacapone and cabergoline as well as their physiologically acceptable salts.

Additionally advantageous is a pharmaceutical composition in which the monoamine oxidase inhibitor is selected from the group consisting of selegiline, moclobemide and tranylcypromine as well as physiologically acceptable salts thereof.

In addition, a pharmaceutical composition is preferred in which the β-hydroxylase inhibitor is selected from calcium 5-butyl picolinate and calcium 5-pentyl picolinate as well as physiologically acceptable salts thereof.

Another subject of the invention is the use of the deuterated catecholamine derivatives according to the invention as well as physiologically acceptable salts thereof for use in the prophylaxis of psychoses, particularly in predisposed patients, for the prophylaxis of a relapse and also particularly for the treatment of acute psychoses, for example, with negative symptomatology.

Particularly preferred is the use of the deuterated catecholamine derivatives according to the invention as well as physiologically acceptable salts thereof, in combination with one or more enzyme inhibitors, for use in the prophylaxis of psychoses and for use in acute psychoses, preferably psychoses with negative symptomatology.

Particularly preferred is the use of the deuterated catecholamine derivatives according to the invention as well as physiologically acceptable salts thereof, if the enzyme inhibitor or the enzyme inhibitors are decarboxylase inhibitors and/or catechol-O-methyltransferase inhibitors and/or monoamine oxidase inhibitors and/or β-hydroxylase inhibitors.

Particularly preferred is the use of the deuterated catecholamine derivatives according to the invention as well as physiologically acceptable salts thereof, if the decarboxylase inhibitor is selected from the group consisting of D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically acceptable salts thereof.

The use of the deuterated catecholamine derivatives according to the invention as well as physiologically acceptable salts thereof is advantageous, if the catechol-O-methyltransferase inhibitor is selected from entacapone and cabergoline as well as physiologically acceptable salts thereof.

In addition, the use of the deuterated catecholamine derivatives according to the invention as well as physiologically acceptable salts thereof is advantageous, if the monoamine oxidase inhibitor is selected from the group consisting of selegiline, moclobemide and tranylcypromine as well as physiologically acceptable salts thereof.

The use of the deuterated catecholamine derivatives according to the invention as well as physiologically acceptable salts thereof is particularly advantageous, if the β-hydroxylase inhibitor is selected from calcium 5-butyl picolinate and calcium 5-pentyl picolinate as well as physiologically acceptable salts thereof.

Another subject of the invention is the use of the deuterated catecholamine derivatives according to the invention as well as physiologically acceptable salts thereof for the production of pharmaceuticals for use in the prophylaxis of psychoses.

Still another subject of the invention is a pharmaceutical composition which contains the deuterated catecholamines according to the invention as well as physiologically acceptable salts thereof for use in the prophylaxis of psychoses and for the treatment of acute psychoses, in addition to pharmaceutically acceptable adjuvants and additives.

Particularly advantageous is a pharmaceutical composition which contains the deuterated catecholamines according to the invention as well as physiologically acceptable salts thereof for the prophylaxis of psychoses and for the therapy of acute psychoses as well as one or more enzyme inhibitors, in addition to pharmaceutically acceptable adjuvants and additives.

Particularly preferred is a pharmaceutical composition in which the enzyme inhibitor or the enzyme inhibitors are decarboxylase inhibitors and/or catechol-O-methyltransferase inhibitors and/or monoamine oxidase inhibitors and/or β-hydroxylase inhibitors.

Additionally advantageous is a pharmaceutical composition in which the decarboxylase inhibitor is selected from the group consisting of D,L-serine 2-(2,3,4-trihydroxybenzyl) hydrazide (benserazide), (−)-L-α-hydrazino-3,4-dihydroxy-α-methylhydrocinnamic acid (carbidopa), L-serine 2-(2,3,4-trihydroxybenzyl) hydrazide, glycine 2-(2,3,4-trihydroxybenzyl) hydrazide and L-tyrosine 2-(2,3,4-trihydroxybenzyl) hydrazide as well as physiologically acceptable salts thereof.

Particularly advantageous is a pharmaceutical composition in which the catechol-O-methyltransferase inhibitor is selected from entacapone and cabergoline as well as physiologically acceptable salts thereof.

Particularly advantageous is a pharmaceutical composition in which the monoamine oxidase inhibitor is selected from the group consisting of selegiline, moclobemide and tranylcypromine as well as physiologically acceptable salts thereof.

Particularly preferred is a pharmaceutical composition in which the β-hydroxylase inhibitor is selected from calcium 5-butyl picolinate and calcium 5-pentyl picolinate as well as physiologically acceptable salts thereof.

The production of the compounds according to the invention is known to one skilled in the art. Analogous production methods are used as described, for example, in DE-A 102 61 807.

For the production of the physiologically acceptable salts of the deuterated catecholamine derivatives according to the invention, the usual physiologically acceptable inorganic and organic acids such as hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid can be used. Additional acids that can be used are described, for example, in Fortschritte der Arzneimittelforschung, Vol. 10, pp. 224-225, Birkhäuser Publishers, Basel and Stuttgart, 1966, and Journal of Pharmaceutical Sciences, Vol. 66, pp. 1-5 (1977).

The acid addition salts are usually obtained in a way known in and of itself by mixing the free base or solutions thereof with the corresponding acid or solutions thereof in an organic solvent, for example, a lower alcohol, such as methanol, ethanol, n-propanol or isopropanol or a lower ketone such as acetone, methyl ethyl ketone or methyl isobutyl ketone or an ether such as diethyl ether, tetrahydrofuran or dioxane. For better crystal precipitation, mixtures of the named solvents can also be used. In addition, physiologically acceptable aqueous solutions of acid addition salts of the compounds used according to the invention can be produced there from in an aqueous acid solution.

The acid addition salts of the compounds according to the invention can be converted to the free base in a way known in and of itself, e.g., with alkalis or ion exchangers. Additional salts can be obtained from the free base by reaction with inorganic or organic acids, particularly those which are suitable for the formation of salts that can be employed therapeutically. These or also other salts of the new compound, such as, e.g., the picrate, may also serve for purification of the free base by converting the free base into a salt, separating this salt, and again releasing the base from the salt.

The subject of the present invention is also pharmaceuticals for oral, buccal, sublingual, nasal, rectal, subcutaneous, intravenous or intramuscular application as well as for inhalation, which, in addition to the usual vehicle and dilution agents, also contain a compound of general formula I or the acid addition salt thereof as an active ingredient.

The pharmaceuticals of the invention are produced, in the known way and with suitable dosage, with the usual solid or liquid vehicle substances or dilution agents and the usually used pharmaceutical-technical adjuvants corresponding to the desired type of application. The preferred preparations consist of a form of administration which is suitable for oral application. Such forms of administration include, for example, tablets, sucking tablets, film tablets, dragees, capsules, pills, powders, solutions, aerosols or suspensions or slow-release forms.

Of course, parenteral preparations such as injection solutions are also considered. In addition, suppositories, for example, have also been named as preparations. Corresponding tablets can be obtained, for example, by mixing the active substance with known adjuvants, for example, inert dilution agents such as dextrose, sugar, sorbitol, mannitol, polyvinylpyrrolidone, bursting agents such as corn starch or alginic acid, binders such as starches or gelantins, lubricants such as magnesium stearate or talc and/or agents for achieving a slow-release effect such as carboxypolymethylene, carboxymethylcellulose, cellulose acetate phthalate or polyvinyl acetate. The tablets may also consist of several layers.

Dragees can also be produced correspondingly, for controlled or delayed release forms of preparation, by coating the cores produced analogously to the tablets with agents commonly used in dragee coatings, for example, polyvinylpyrrolidone or shellac, gum arabic, talc, titanium dioxide or sugar. The dragee envelope may also consist of several layers, wherein the adjuvants mentioned above in the case of tablets can be used.

Solutions or suspensions containing the active substance used according to the invention may additionally contain agents that improve taste, such as saccharin, cyclamate or sugar, as well as, e.g., taste enhancers such as vanilla or orange extract. They may also contain suspension adjuvants such as sodium carboxymethylcellulose or preservatives such as p-hydroxybenzoate. Capsules containing active substances can be produced, for example, by mixing the active substance with an inert vehicle such as lactose or sorbitol and encapsulating this mixture in gelatin capsules. Suitable suppositories can be produced, for example, by mixing with vehicle agents provided therefore, such as neutral fats or polyethylene glycol or derivatives thereof.

The production of the pharmaceutical preparations according to the invention is known in and of itself, and is described in handbooks known to the person skilled in the art, for example, Hager's Handbuch [Handbook] (5th ed.) 2, 622-1045; List et al., Arzneiformenlehre [Instructions for Drug Forms], Stuttgart: Wiss.Verlagsges. 1985; Sucker et al., Pharmazeutische Technologie [Pharmaceutical Technology], Stuttgart: Thieme 1991; Ullmann's Enzyklopädie [Encyclopedia] (5th ed.) A 19, 241-271; Voigt, Pharmazeutische Technologie [Pharmaceutical Technology], Berlin: Ullstein Mosby 1995.

As known from WO-A 2004/056724, L-2-Amino-2,3,3-trideutero-3-(3,4-dihydroxyphenyl) propionic acid is a selectively deuterated L-DOPA derivative with better pharmacokinetic and pharmacodynamic properties when compared to L-DOPA. Administration of L-2-Amino-2,3,3-trideutero-3-(3,4-dihydroxyphenyl) propionic acid to male Wistar rats increased dopamine in the striatum significantly more compared to non-deuterated L-DOPA.

It has been surprisingly found that L-2-Amino-2,3-dideutero-3-(3,4-dihydroxyphenyl) propionic acid increased dopamine in the striatum significantly more than L-2-Amino-2,3,3-trideutero-3-(3,4-dihydroxyphenyl) propionic acid, although the compound has less deuterium at the beta position of the side chain of its molecule (Example 15 and Table 1).

Furthermore, whereas L-2-Amino-2,3,3-trideutero-3-(3,4-dihydroxyphenyl) propionic acid reduces the striatal output of norepinephrine compared to L-DOPA, L-2-Amino-2,3-dideutero-3-(3,4-dihydroxyphenyl) propionic acid does not block the formation of norepinephrine.

Therefore, L-2-Amino-2,3-dideutero-3-(3,4-dihydroxyphenyl) propionic acid has two advantages, it provides more dopamine and enough norepinephrine which has been shown to play an important role in compensating for the loss in dopaminergic function (Archer and Fredriksson, 2006, Neural Transm., 113(9): 1119-29; Cathala et al. 2002, Neuroscience, 115(4): 1059-65; Tong et al. 2006, Arch Neurol, 63(12): 1724-8).

The highly soluble L-DOPA methyl ester has been shown to function as a prodrug of L-DOPA. In animal experiments, L-DOPA methyl ester given orally or intraperitoneally was equivalent on a molar basis to L-DOPA. However, therapeutic equivalence was not maintained with continuous intravenous infusion in Patients with Parkinson's disease exhibiting severe on-off phenomena. The optimal infusion rate for L-DOPA methyl ester was 2.7 times that required for L-DOPA (Stocchi et al. 1992, Movement Disorders, 7: 249-256). Surprisingly, L-2-Amino-2,3-dideutero-3-(3,4-dihydroxyphenyl) propionic acid methyl ester is therapeutically equivalent to L-2-Amino-2,3-dideutero-3-(3,4-dihydroxyphenyl) propionic acid during continuous intravenous infusion.

The following examples are given to explain the present invention in more detail but shall not be understood to limit the scope of the invention.

EXAMPLE 1

D,L-2-Amino-2-deutero-3-(3,4-dihydroxyphenyl) propionic acid 2.5 g Levodopa are dissolved in 60 mL $CH_3CO_2D$ under argon and then reacted with 0.25 mL benzaldehyde under reflux. Following elimination of acetic acid and benzaldehyde by distillation in vacuum, 2 mL of methanol are added. The product is precipitated slowly with 10 mL ethyl acetate/toluene (1:1). After drying under vacuum, 2.2 g D,L-2-Amino-2-deutero-3-(3,4-dihydroxyphenyl) propionic acid are isolated.

Yield: 87.6%

EXAMPLE 2

D,L-2-Amino-2-deutero-3-(3,4-dihydroxyphenyl) methyl propionate 2.0 g of D,L-2-Amino-2-deutero-3-(3,4-dihydroxyphenyl) propionic acid are dissolved in 30 mL methanol and cooled to −10° C. and reacted dropwise with 1 ml of thionyl chloride. The reaction batch is then heated to 40° C. for 15-hours. The volatile substances in the reaction batch are eliminated in vacuum and 10 ml of water and 15 ml of a solution of 0.8 g of sodium hydrogen carbonate, 1 g of sodium sulfate and 1 mg of ascorbic acid are added. The pH of the solution is adjusted to a value of 7 by addition of a dilute sodium hydroxide solution. The product is transferred to the organic phase by extraction with oxygen-free ethyl acetate, which contains 0.01% 2,6-ditert-butyl-4-methoxyphenol. The organic phase is dried and then the solvent is distilled off. 50 ml of oxygen-free diethyl ether are added to the residue and after this material is left to stand overnight, the D,L-2-amino-2-deutero-3-(3,4-dihydroxyphenyl)methyl propionate precipitates. After recrystallization from an oxygen-free methanol/diethyl ether mixture, which is combined with 2,6-di-tert-butyl-4-methoxyphenol, 1.8 g of product is isolated.

Yield: 84.9%

EXAMPLE 3

L-2-Amino-2-deutero-3-(3,4-dihydroxyphenyl) propionic acid 1.15 g of D,L-2-Amino-2-deutero-3-(3,4-dihydroxyphenyl)methyl propionate are dissolved in 30 mL of a 0.2-molar sodium bicarbonate solution (pH 8.2). 200 µL of alcalase are added and the pH of the solution is kept at this value by means of carbonate-bicarbonate buffer. The course of the reaction is monitored by HPLC and the reaction is terminated by the addition of hydrochloric acid when the concentration of the propionate ester has been reduced to one-half. The deuterated amino acid contained in the solution is separated from the deuterated methyl ester chromatographically by use of the solvent system of acetonitrile/0.1% aqueous trifluoroacetic acid (15:85) and 0.51 g of L-2-amino-2-deutero-3-(3,4-dihydroxyphenyl) propionic acid is isolated.

Yield: 95% (based on the proportion of L-enantiomer)

Melting point: 287-290° C.

$C_9H_{10}NO_4D$:

calc. C, 54.54%; H, 5.09%; N, 7.07%; O, 32.29%; D, 1.02%.

found C, 54.45%; H+D, 6.08; N, 7.02.

$^1$H-NMR (400 MHz, d6-DMSO): 6.58 (d, 1H); 6.54 (s, 1H); 6.47 (d, 1H); 3.07 (d, 1H); 2.90 (d, 1H)

EXAMPLE 4

L-2-Amino-2-deutero-3-(3,4-dihydroxyphenyl)methyl propionate 2.0 g of L-2-Amino-2-deutero-3-(3,4-dihydroxyphenyl) propionic acid are dissolved in 30 mL methanol are cooled to −10° C. and reacted dropwise with 1 ml of thionyl chloride. The reaction batch is then heated to 40° C. for 15 hours. The volatile substances in the reaction batch are eliminated in vacuum and 10 ml of water and 15 ml of a solution of 0.8 g of sodium hydrogen carbonate, 1 g of sodium sulfate and 1 mg of ascorbic acid are added. The pH of the solution is adjusted to a value of 7 by addition of a dilute sodium hydroxide solution. The product is transferred to the organic phase by extraction with oxygen-free ethyl acetate, which contains 0.01% 2,6-ditert-butyl-4-methoxyphenol. The organic phase is dried and then the solvent is distilled off. 50 ml of oxygen-free diethyl ether are added to the residue, and after the material is left to stand overnight, the L-2-amino-2-deutero-3-(3,4-dihydroxyphenyl)methyl propionate precipitates. After recrystallization from an oxygen-free methanol/diethyl ether mixture, which is combined with 2,6-di-tert-butyl-4-methoxyphenol, 1.9 g of product is isolated.

Yield: 89.6%

$C_{10}H_{12}NO_4D$:

calc. C, 56.60%; H, 5.70%; N, 6.60%: O, 30.16%; D, 0.95%.

found C, 56.65%; H+D, 6.63%; N, 6.54%.

$^1$H-NMR (400 MHz, d6-DMSO): 6.58 (d, 1H); 6.54 (s, 1H); 6.47 (d, 1H); 3.81 (s, 3H); 3.07 (d, 1H); 2.90 (d, 1H)

EXAMPLE 5

L-2-Amino-2-deutero-3-(3,4-dihydroxyphenyl)ethyl propionate 2.0 g of L-2-Amino-2-deutero-3-(3,4-dihydroxyphenyl) propionic acid are dissolved in 30 mL ethanol are cooled to −10° C. and reacted dropwise with 1 ml of thionyl chloride. The reaction batch is then heated to 40° C. for 15 hours. The volatile substances in the reaction batch are eliminated in vacuum and 10 ml of water and 15 ml of a solution of 0.8 g of sodium hydrogen carbonate, 1 g of sodium sulfate and 1 mg of ascorbic acid are added. The pH of the solution is adjusted to a value of 7 by addition of a dilute sodium hydroxide solution. The product is transferred to the organic phase by extraction with oxygen-free ethyl acetate, which contains 0.01% 2,6-ditert-butyl-4-methoxyphenol. The organic phase is dried and then the solvent is distilled off. 50 ml of oxygen-free diethyl ether are added to the residue, and after the material is left to stand overnight, the L-2-amino-2-deutero-3-(3,4-dihydroxyphenyl)ethyl propionate precipitates. After recrystallization from an oxygen-free ethanol/diethyl ether mixture, which is combined with 2,6-ditert-butyl-4-methoxyphenol, 2 g of product is isolated.

Yield: 88.5%

$C_{11}H_{14}NO_4D$:

calc. C, 58.40%; H, 6.24%; N, 6.19%; O, 28.29%; D, 0.89%.

found C, 58.32%; H+D, 7.03%; N, 6.12%.

$^1$H-NMR (400 MHz, d6-DMSO): 6.58 (d, 1H); 6.54 (s, 1H); 6.47 (d, 1H); 4.15 (q, 2H); 3.07 (d, 1H); 2.90 (d, 1H); 1.21 (t, 3H)

EXAMPLE 6

L-2-Amino-2,3(S)-dideutero-3-(3,4-dihydroxyphenyl) propionic acid 2.5 g of N-acetyl-3-methoxy-4-acetoxy cinnamic acid are dissolved in 30 mL methanol containing 0.027 g sodium hydroxide and placed into an autoclave. The oxygen is replaced by nitrogen before the reactor is filled with deuterium gas. At the same time 0.5 g of Monsanto catalyst are prepared in 2.5 mL toluene by treating with deuterium gas. After addition of the catalyst to the autoclave, the "hydrogenation" is started at 60° C. and 4-5 bar. After 4 hours, the excess of deuterium gas is removed and the solvent is distilled of. The sodium salt of the deuterated product is isolated and recrystallized.

Yield: 2.4 g (94%)

0.9 g of the sodium salt are dissolved in 2.5 mL of hydrobromic acid (23%) and heated to reflux at about 105-110° C. Afterwards, the reaction mixture is cooled to 25-30° C. and the pH is adjusted to 3 by addition of concentrated sodium hydroxide solution to start the precipitation of L-2-Amino-2,3(S)-dideutero-3-(3,4-dihydroxyphenyl) propionic acid. The precipitate is washed with cold water and recrystallized in hot water under protective gas. After recrystallization, 0.51 g of the product are isolated.

Yield: 85.1%

Melting point: 286-299° C.

$C_9H_9NO_4D_2$:
calc. C, 54.27%; H, 4.55%; N, 7.03%; O, 32.13%; D, 2.02%.
found C, 54.15%; H+D, 6.50%; N, 7.08%.
$^1$H-NMR (400 MHz, d6-DMSO): 6.59 (d, 1H); 6.54 (s, 1H); 6.48 (d, 1H); 2.74 (m, 1H)

EXAMPLE 7

L-2-Amino-2,3(S)-dideutero-3-(3,4-dihydroxyphenyl)methyl propionate

The compound is produced according to the description for the mono-deuterated compound (cf. example 4).
Yield: 91%
$C_{10}H_{11}D_2NO_4$:
calc. C, 56.33%; H, 5.20%; N, 6.57%; O, 30.01%; D, 1.89%.
found C, 56.22%; H+D, 7.01; N, 6.45.
$^1$H-NMR. (400 MHz, d6.-DMSO): 6.59 (d, 1H); 6.54 (S, 1H); 6.48 (d, 1H); 2.72 (m, 1H); 3.81 (s, 3H).

EXAMPLE 8

L-2-Amino-2,3(S)-dideutero-3-(3,4-dihydroxyphenyl)ethyl propionate

The compound is produced according to the description for the mono-deuterated compound (cf. example 5).
Yield: 93%,
$C_{11}H_{13}D_2NO_4$:
calc. C, 58.14%; H, 5.77%; N, 6.16%; O, 28.16%; D, 1.77%.
found C, 58.10%; H+D, 7.48%; N, 6.10%.
$^1$H-NMR (400 MHz, d6-DMSO): 6.59 (d, 1H); 6.54 (s, 1H); 6.48 (d, 1H); 2.72 (m, 1H); 4.17 (q, 2H); 1.22 (t, 3H).

EXAMPLE 9

L-2-Amino-2-deutero-3-(2,3,6-trideutero-4,5-dihydroxyphenyl) propionic acid 0.2 g of L-2-Amino-2-deutero-3-(3,4 dihydroxyphenyl) propionic acid are placed into an autoclave and 10 mL of $D_2O$ are added. The autoclave is evacuated and heated to 190° C. for 24 hours. The solvent is eliminated and acetic acid ethyl ester is added. The solvent is distilled of and the residue washed with cold acetone. Thereafter, 0.17 g of the product are isolated.
Yield: 84%
$C_9H_7NO_4D_4$:
calc. C, 53.72%; H, 3.51%: N, 6.96%; O, 31.81%; D, 4.00%.
found C, 53.65%; H+D, 7.45%; N, 6.90%.
$^1$H-NMR (400 MHz, d6-DMSO): 3.06 (d, 1H); 2.88 (d, 1H)

EXAMPLE 10

L-2-Amino-2-deutero-3-(2,3,6-trideutero-4,5-dihydroxyphenyl)methyl propionate

The compound is produced according to the description for the mono-deuterated compound (cf. example 4).
Yield: 89%.
$C_{10}H_9NO_4D_4$:
calc. C, 55.80%; H, 4.21%; N, 6.51%; O, 29.73%; D, 3.74%.
found C, 55.71%; H+D, 7.89%; N, 6.53%.
$^1$H-NMR (400 MHz, d6-DMSO): 3.81 (s, 3H); 3.08 (d, 1H); 2.88 (d, 1H)

EXAMPLE 11

L-2-Amino-2-deutero-3-(2,3,6-trideutero-4,5-dihydroxyphenyl)ethyl propionate

The compound is produced according to the description for the mono-deuterated compound (cf. example 5).
Yield: 92%.
$C_{11}H_{11}NO_4D_4$:
calc. C, 57.63%; H, 4.84%; N, 6.11%; O, 27.91%; D, 3.51%.
found C, 57.57%; H+D, 8.31%; N, 6.15%.
$^1$H-NMR (400 MHz, d6-DMSO): 4.17 (q, 2H); 3.06 (d, 1H); 2.88 (d, 1H); 1.21 (t, 3H)

EXAMPLE 12

L-2-Amino-2,3-dideutero-3-(2,3,6-trideutero-4,5-dihydroxyphenyl) propionic acid 0.2 g of L-2-Amino-2-deutero-3-(3,4-dihydroxyphenyl) propionic acid are placed into an autoclave and 10 mL of $D_2O$ are added. The autoclave is evacuated and heated to 190° C. for 24 hours. The solvent is eliminated and acetic acid ethyl ester is added. The solvent is distilled of and the residue washed with cold acetone. Thereafter, 0.16 g of the product are isolated.
Yield: 79.2%
$C_9H_6NO_4D_5$:
calc. C, 53.46%; H, 2.99%; N, 6.93%; O, 31.65%; D, 4.98%.
found C, 53.49%; H+D, 7.92%; N, 6.88%.
$^1$H-NMR (400 MHz, d6-DMSO): 2.76 (m, 1H)

EXAMPLE 13

L-2-Amino-2,3-dideutero-3-(2,3,6-trideutero-4,5-dihydroxyphenyl)methyl propionate The compound is produced according to the description for the mono-deuterated compound (cf. example 4).
Yield: 90%
$C_{11}H_8D_5NO_4$:
calc. C, 55.54%; H, 3.73%; N, 6.48%; O, 29.59%; D, 4.66%.
found C, 55.50%; H+D, 8.31; N, 6.45%.
$^1$H-NMR (400 MHz, d6-DMSO): 3.80 (s, 3H); 2.74 (m, 1H)

EXAMPLE 14

L-2-Amino-2,3-dideutero-3-(2,3,6-trideutero-4,5-dihydroxyphenyl)ethyl propionate The compound is produced according to the description for the mono-deuterated compound (cf. example 5).
Yield: 93%
$C_{11}H_{10}D_5NO_4$:
calc. C, 57.38%; H, 4.38%; N, 6.08%; O, 27.79%; D, 4.37%.
found C, 57.34%; H+D, 8.71%; N, 6.04%.
$^1$H-NMR (400 MHz, d6-DMSO): 4.15 (q, 2H); 2.75 (m, 1H); 1.21 (t, 3H)

EXAMPLE 15

Striatal Dopamine Output Measured by Microdialysis

The striatal output of dopamine was measured in Male Wistar rats following intraperitoneal administration of 50 mg/kg L-2-Amino-3-(3,4-dihydroxyphenyl) propionic acid (L-DOPA), L-2-Amino-2,3,3-trideutero-3-(3,4-dihydroxyphenyl) propionic acid (WO-A 2004/056724, Example 6) and L-2-Amino-2,3-dideutero-3-(3,4-dihydroxyphenyl) propionic acid (Example 6), respectively. Male wistar rats (BK Universal, Sollentuna, Sweden) weighing about 300 g at the time of experiment were anaesthetized with a cocktail containing fentanyl citrate (0.39 mg/kg) and fluanisone (12.5 mg/kg, Hypnorm®, Janssen-Cilag) and midazolam (6.25 mg/kg, Dormicum®, Roche) diluted in distilled water (1:1:2; 5 ml/kg i.p.) and mounted in a stereotaxic frame. Dialysis probes were implanted in the dorsolateral striatum (AP: +0.6: ML+3.0: DV −6.2 relative to bregma and the dural surface according to the atlas of Paxinos and Watson (1998)). Dialysis occurs through a semipermeable membrane (Filtral AN69, Hospal Industrie, France) with an active surface length of 3.5 mm. Dialysis experiments were conducted approximately 48 h after surgery in freely moving rats. The rats received 30 min before administration of test items 10 mg/kg Carbidopa, (i.p.). The dialysis probe was perfused with a physiological perfusion solution (Apoteksbolaget, Sweden) at a rate of 2.5 ml/min set by a microinfusion pump (Harvard Apparatus, Holliston, Mass.). Dialysate was collected over 15 min intervals and automatically injected into a high performance liquid chromatography (HPLC) system. On-line quantification of dopamine in the dialysate was accomplished by electrochemical detection (ESA, Chelmsford, Mass.). The location of microdialysis probes was verified in slices of formalin-fixed tissue stained with neutral red. The baseline corrected concentrations (fmol/min) were plotted over the time.

Comparison of $AUC_{0-t}$ (area under the curve) values revealed that the increase of dopamine in the striatum following administration of 50 mg/kg L-2-Amino-2,3,3-trideutero-3-(3,4-dihydroxyphenyl) propionic acid was about twice as high compared to L-2-Amino-3-(3,4-dihydroxyphenyl) propionic acid (L-DOPA) as displayed in Table 1. The increase of striatal dopamine following administration of 50 mg/kgL-2-Amino-2,3-dideutero-3-(3,4-dihydroxyphenyl) propionic acid (Example 6) was even threefold higher than that measured after administration of L-DOPA.

TABLE 1

Baseline corrected dopamine output in the striatum

| Compound | $AUC_{0-t}$ [fmol/min*min] |
|---|---|
| L-2-Amino-3-(3,4-dihydroxyphenyl) propionic acid | 228 |
| L-2-Amino-2,3,3-trideutero-3-(3,4-dihydroxyphenyl) propionic acid | 533 |
| L-2-Amino-2,3-dideutero-3-(3,4-dihydroxyphenyl) propionic acid (Ex. 6) | 685 |

The invention claimed is:

1. Deuterated catecholamine derivatives of the general formula I

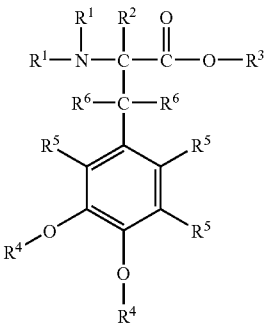

Formula I $R^1$ is H or D, or a group that is easily hydrolytically or enzymatically cleavable under physiological conditions,
$R^2$ indicates D,
$R^3$ is H, D, $C_1$ to $C_6$ alkyl or $C_1$ to $C_6$-cycloalkyl, deuterated to $C_1$ to $C_6$ wherein alkyl or $C_1$ to $C_6$-cycloalkyl, or a group that is easily hydrolytically or enzymatically cleavable under physiological conditions,
$R^4$ indicates H or D, or a group that is easily hydrolytically or enzymatically cleavable under physiological conditions,
$R^5$ is H or D, and
one of $R^6$ is H and the other $R^6$ is D,
as well as their physiologically acceptable salts and their stereoisomers, enantiomeres or diastereomers in optically pure form.

2. Deuterated catecholamine derivatives according to claim 1, wherein
$R^1$ is H or D,
$R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D, and
$R^5$ is D.

3. Deuterated catecholamine derivatives according to claim 1, wherein
$R_1$ is H or D,
$R^3$ is D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D, and
$R^5$ is D.

4. Deuterated catecholamine derivatives according to claim 1, wherein
$R_1$ is H or D,
$R^3$ is H, D, $C_1$ to $C_6$-alkyl or $C_5$ to $C_6$-cycloalkyl, deuterated $C_1$ to $C_6$-alkyl or deuterated $C_5$ to $C_6$-cycloalkyl,
$R^4$ indicates H or D, and
$R^5$ is D.

5. Deuterated catecholamine derivatives according to the general formula I, wherein
$R_1$ is H or D,
$R^3$ is $C_1$ to $C_6$-alkyl or $C_5$ to $C_6$-cycloalkyl,
$R^4$ indicates H or D, and
$R^5$ is D.

6. Deuterated catecholamine derivatives according to claim 1, wherein
$R_1$ is H or D,
$R^3$ is methyl,
$R^4$ indicates H or D, and
$R^5$ is D.

7. Deuterated catecholamine derivatives according to claim 1, wherein $R^1$ is H or D,
$R^3$ is ethyl,
$R^4$ indicates H or D, and
$R^5$ is D.

8. Deuterated catecholamine derivatives according to claim 1, wherein
$R^1$ is H or D,
$R^3$ is perdeuteroethyl,
$R^4$ indicates H or D, and
$R^5$ is D.

9. Deuterated catecholamine derivatives according to claim 1, wherein
$R^1$ is H or D,
$R^3$ is perdeuteroethyl,
$R^4$ indicates H or D, and
$R^5$ is D.

10. Deuterated catecholamine derivatives according to claim 1, wherein
$R^1$ is H or D,
$R^3$ is perdeuteroethyl,
$R^4$ indicates D, and
$R^5$ is H or D.

11. Deuterated catecholamine derivatives according to claim 1, namely
R/R-2-amino-2,3-dideutero-3-(3,4-dihydroxyphenyl)propionic acid,
R/R-2-amino-2,3-dideutero-3-(3,4-dihydroxyphenyl)propionic acid methyl ester,
R/R-2-amino-2,3-dideutero-3-(3,4-dihydroxyphenyl)propionic acid ethyl ester,
R/S-2-amino-2,3-dideutero-3-(3,4-dihydroxyphenyl)propionic acid,
R/S-2-amino-2,3-dideutero-3-(3,4-dihydroxyphenyl)propionic acid methyl ester,
R/S-2-amino-2,3-dideutero-3-(3,4-dihydroxyphenyl)propionic acid ethyl ester,
S/R-2-amino-2,3-dideutero-3-(3,4-dihydroxyphenyl)propionic acid,
S/R-2-amino-2,3-dideutero-3-(3,4-dihydroxyphenyl)propionic acid methyl ester,
S/R-2-amino-2,3-dideutero-3-(3,4-dihydroxyphenyl)propionic acid ethyl ester,
S/S-2-amino-2,3-dideutero-3-(3,4-dihydroxyphenyl)propionic acid,
S/S-2-amino-2,3-dideutero-3-(3,4-dihydroxyphenyl)propionic acid methyl ester,
S/S-2-amino-2,3-dideutero-3-(3,4-dihydroxyphenyl)propionic acid ethyl ester,
2-amino-2,3-dideutero-3-(2,3,6-trideutero-4,5- dihydroxyphenyl) propionic acid,
2-amino-2,3-dideutero-3-(2,3,6-trideutero-4,5- dihydroxyphenyl) propionic acid methyl ester,
2-amino-2,3-dideutero-3-(2,3,6-trideutero-4,5- dihydroxyphenyl) propionic acid ethyl ester,
R/R-2-amino-2,3-dideutero-3-(2,3,6-trideutero-4,5- dihydroxyphenyl) propionic acid,
R/R-2-amino-2,3-dideutero-3-(2,3,6-trideutero-4,5- dihydroxyphenyl) propionic acid methyl ester,
R/R-2-amino-2,3-dideutero-3-(2,3,6-trideutero-4,5- dihydroxyphenyl) propionic acid ethyl ester,
R/S-2-amino-2,3-dideutero-3-(2,3,6-trideutero-4,5- dihydroxyphenyl) propionic acid,
R/S-2-amino-2,3-dideutero-3-(2,3,6-trideutero-4,5-dihydroxyphenyl) propionic acid methyl ester,
R/S-2-amino-2,3-dideutero-3-(2,3,6-trideutero-4,5- dihydroxyphenyl) propionic acid ethyl ester,
S/R-2-amino-2,3-dideutero-3-(2,3,6-trideutero-4,5- dihydroxyphenyl) propionic acid,
S/R-2-amino-2,3-dideutero-3-(2,3,6-trideutero-4,5- dihydroxyphenyl) propionic acid methyl ester,
S/R-2-amino-2,3-dideutero-3-(2,3,6-trideutero-4,5- dihydroxyphenyl) propionic acid ethyl ester,
S/S-2-amino-2,3-dideutero-3-(2,3,6-trideutero-4,5- dihydroxyphenyl) propionic acid,
S/S-2-amino-2,3-dideutero-3-(2,3,6-trideutero-4,5- dihydroxyphenyl) propionic acid methyl ester, and
S/S-2-amino-2,3-dideutero-3-(2,3,6-trideutero-4,5- dihydroxyphenyl) propionic acid ethyl ester.

12. A pharmaceutical composition, which contains deuterated catecholamines according to claim 1 as well as physiologically acceptable salts thereof, for the treatment of Parkinson's disease, of restless leg syndrome, of dystonia, for inhibiting prolactin secretion, for stimulating the release of growth hormone, for the treatment of neurological symptoms of chronic manganese intoxications, of amyotrophic lateral sclerosis and of multiple system atrophy, in addition to pharmaceutically acceptable adjuvants and additives.

13. A pharmaceutical composition, which contains deuterated catecholamines according to claim 1 as well as physiologically acceptable salts thereof, for the treatment of Parkinson's disease, restless leg syndrome, dystonia, for inhibiting prolactin secretion, for stimulating the release of growth hormone, for the treatment of neurological symptoms of chronic manganese intoxications, of amyotrophic lateral sclerosis and of multiple system atrophy, as well as one or more enzyme inhibitors, in addition to pharmaceutically acceptable adjuvants and additives.

14. The pharmaceutical composition according to claim 13, further characterized in that the enzyme inhibitor or the enzyme inhibitors involve decarboxylase inhibitors and/or catechol-0-methyltransferase inhibitors and/or monoamine oxidase inhibitors and/or β-hydroxylase inhibitors.

15. The pharmaceutical composition according to claim 13, further characterized in that the decarboxylase inhibitor is selected from the group consisting of D,L-serine 2-(2,3,4-trihydroxybenzyl) hydrazide (benserazide), (−)-L-α-hydrazino-3,4 dihydroxy-α-methylhydrocinnamic acid (carbidopa), L serine 2- (2,3,4-trihydroxybenzyl) hydrazide, glycine 2-(2,3,4- trihydroxybenzyl) hydrazide and L-tyrosine 2 (2,3,4- trihydroxybenzyl) hydrazide as well as physiologically acceptable salts thereof.

16. The pharmaceutical composition according to claim 14, further characterized in that the catechol-0- methyltransferase inhibitor is selected from entacapone and cabergoline as well as physiologically acceptable salts thereof.

17. The pharmaceutical composition according to claim 14, further characterized in that the monoamine oxidase inhibitor is selected from the group consisting of selegiline, moclobemide and tranylcypromine as well as physiologically acceptable salts thereof.

18. The pharmaceutical composition according to claim 14, further characterized in that the β-hydroxylase inhibitor is selected from calcium 5-butyl picolinate and calcium 5-pentyl picolinate as well as physiologically acceptable salts thereof.

* * * * *